United States Patent
Okumura

(10) Patent No.: US 10,893,841 B2
(45) Date of Patent: Jan. 19, 2021

(54) RADIOGRAPHY APPARATUS

(71) Applicant: Shimadzu Corporation, Kyoto (JP)

(72) Inventor: Hiroshi Okumura, Otsu (JP)

(73) Assignee: Shimadzu Corporation, Kyoto (JP)

( * ) Notice: Subject to any disclaimer, the term of this patent is extended or adjusted under 35 U.S.C. 154(b) by 123 days.

(21) Appl. No.: 15/760,801

(22) PCT Filed: Sep. 17, 2015

(86) PCT No.: PCT/JP2015/076579
§ 371 (c)(1),
(2) Date: Mar. 16, 2018

(87) PCT Pub. No.: WO2017/046929
PCT Pub. Date: Mar. 23, 2017

(65) Prior Publication Data
US 2018/0249971 A1  Sep. 6, 2018

(51) Int. Cl.
*A61B 6/08* (2006.01)
*A61B 6/00* (2006.01)
(Continued)

(52) U.S. Cl.
CPC .............. *A61B 6/08* (2013.01); *A61B 6/06* (2013.01); *A61B 6/4494* (2013.01); *A61B 6/54* (2013.01); *G21K 1/02* (2013.01)

(58) Field of Classification Search
CPC .......... A61B 6/08; A61B 6/06; A61B 6/4494; A61B 6/54; G21K 1/02
(Continued)

(56) References Cited

U.S. PATENT DOCUMENTS 4,416,022 A * 11/1983 Cutter ................ A61B 6/587
378/206
4,811,374 A *  3/1989 Kasa ...................... H05G 1/30
378/110
(Continued)

FOREIGN PATENT DOCUMENTS

JP     2005-304696 A    11/2005
JP     2012-055421 A     3/2012
JP     2013-183959 A     9/2013

OTHER PUBLICATIONS

International Search Report for PCT Application PCT/JP2015/07659, dated Sep. 17, 2015.

*Primary Examiner* — Blake C Riddick
(74) *Attorney, Agent, or Firm* — Muir Patent Law, PLLC

(57) ABSTRACT

The radiography apparatus of the present invention includes a CPU 71 having a function of a lighting time limitation means to control the lighting time of light sources in such a way as to maintain a temperature at or below a predetermined temperature. In order to discriminate the type of light source connected to the device body, the setting of No. 5 pin on the CPU 71 to a high logic state or a low logic state is detected. This enables the detection of whether the light source connected to a control board 70 is a halogen lamp H or a light emitting diode (LED) L. Thus, the type of the light source is discriminated. The CPU 71 changes the controlled limiting lighting time based on the result of discrimination. This prevents the risk of incorrectly carrying out settings and enables the automatic setting for switching light sources.

16 Claims, 5 Drawing Sheets

(51) Int. Cl.
*A61B 6/06* (2006.01)
*G21K 1/02* (2006.01)

(58) Field of Classification Search
USPC .......................................... 378/62, 91, 147
See application file for complete search history.

(56) References Cited

U.S. PATENT DOCUMENTS

| | | | | |
|---|---|---|---|---|
| 4,914,683 | A * | 4/1990 | Tanaka | H05G 1/66 378/101 |
| 5,553,115 | A * | 9/1996 | Odaka | A61B 6/08 378/170 |
| 5,584,292 | A * | 12/1996 | Cheung | A61B 6/4233 378/37 |
| 5,804,832 | A * | 9/1998 | Crowell | G01T 1/24 250/370.09 |
| 6,118,844 | A * | 9/2000 | Fischer | G01B 15/02 378/44 |
| 6,337,750 | B1 * | 1/2002 | Mizoguchi | H04N 1/00241 358/475 |
| 6,426,997 | B1 * | 7/2002 | Fuchs | H01J 35/025 378/117 |
| 7,303,132 | B2 * | 12/2007 | Knowles | G02B 26/10 235/462.01 |
| 2002/0045801 | A1 * | 4/2002 | Niida | A61B 1/00055 600/118 |
| 2003/0010925 | A1 * | 1/2003 | Watanabe | G01T 1/2928 250/370.15 |
| 2003/0086523 | A1 * | 5/2003 | Tashiro | A61B 6/4233 378/19 |
| 2003/0118148 | A1 * | 6/2003 | Kataoka | G01J 3/443 378/44 |
| 2003/0161441 | A1 * | 8/2003 | Stevanovic | G03B 42/08 378/206 |
| 2003/0198317 | A1 * | 10/2003 | Nakagawa | A61B 6/4405 378/62 |
| 2004/0227102 | A1 * | 11/2004 | Kurt | G01N 21/95684 250/491.1 |
| 2005/0226384 | A1 * | 10/2005 | Domoto | H05G 1/56 378/125 |
| 2006/0071170 | A1 * | 4/2006 | Broennimann | H01L 27/14661 250/370.09 |
| 2006/0233306 | A1 * | 10/2006 | Kitami | H05G 1/66 378/131 |
| 2011/0075908 | A1 * | 3/2011 | Kanagawa | A61B 6/4233 382/131 |
| 2012/0130238 | A1 * | 5/2012 | Muraoka | A61B 6/4233 600/436 |
| 2012/0261583 | A1 * | 10/2012 | Watson | H04N 5/32 250/369 |
| 2013/0039465 | A1 * | 2/2013 | Okuno | A61B 6/08 378/62 |
| 2014/0110595 | A1 * | 4/2014 | Iwakiri | H04N 5/32 250/394 |
| 2014/0254760 | A1 * | 9/2014 | Hiroike | A61B 6/4233 378/62 |
| 2015/0098552 | A1 * | 4/2015 | Draper | H05G 1/06 378/142 |
| 2015/0246205 | A1 * | 9/2015 | Schaeffer | A61B 1/05 604/95.04 |
| 2016/0165202 | A1 * | 6/2016 | Lee | H04N 5/2258 348/164 |
| 2016/0334535 | A1 * | 11/2016 | Dreiseitel | G01V 5/005 |

* cited by examiner

RADIOGRAPHY APPARATUS

TECHNICAL FIELD

The present invention relates to a radiography apparatus equipped with a radiation irradiation means for irradiating radiation toward a subject, and more particularly to a technique for controlling an irradiation field of radiation.

BACKGROUND ART

The following explanation will be made by exemplifying an X-ray as a radiation and exemplifying an X-ray image capturing apparatus for performing X-ray image capturing as a radiography apparatus. The X-ray image capturing apparatus is equipped with an X-ray tube (radiation irradiation means) for irradiating an X-ray toward a subject, and is also equipped with a collimator (X-ray diaphragm) for controlling the X-ray irradiation area from the X-ray tube by leaves, and an X-ray detector (an X-ray film, a CR (computed radiography), or an FPD (Flat Panel Detector)) for detecting the X-ray transmitted through the subject via the collimator.

In a collimator for controlling an X-ray irradiation area from an X-ray tube by leaves, the irradiation field of a rectangular X-ray formed by the collimator can be adjusted in lengths of the two sides by, for example, a longitudinal dimension adjustment knob and a lateral dimension adjustment knob provided on the panel surface of the collimator. However, doing this adjustment by monitoring while irradiating the X-ray on the subject before the X-ray image capturing results in increased exposure of the subject.

Therefore, in order to prevent such exposure, a collimator normally has a built-in irradiation field lamp (collimator lamp) which is used as a light source and has a function to irradiate visible light (hereinafter abbreviated as "light") instead of an X-ray. It is possible to adjust the position and the size of the irradiation field before image capturing without irradiating an X-ray by confirming the irradiation field of the light adjusted to match the irradiation field of the X-ray. Lighting of the collimator lamp for irradiating the light is performed by the lighting button. For example, when the lighting button is pressed once, the collimator lamp is configured to be automatically turned off when a predetermined time (for example, 30 seconds) has elapsed.

To continuously light the collimator lamp beyond the predetermined time, the lighting button is pressed multiple times. Specifically, by repeating the pressing of the lighting button again immediately after elapsing of the predetermined time and lighting-off of the collimator lamp, the collimator lamp can be made to continuously light even if the predetermined time has elapsed.

The collimator lamp uses a halogen lamp with large heat generation. When the collimator lamp is lighted for a long time beyond the predetermined time, there is a risk that the temperature of the device exterior will rise due to the heat generation from the halogen lamp to cause overheating. Under the circumstance, the present applicant proposed an X-ray image capturing apparatus in which the temperature limitation is performed by limiting the lighting time of the collimator lamp so as not to exceed a set temperature (see, for example, Patent Document 1).

Specifically, as shown in FIG. 3 of Patent Document 1: Japanese Unexamined Patent Application Publication No. 2012-55421, the control unit is equipped with a storage unit, a pseudo temperature counter, and a lighting control unit. The storage unit stores the temperature rise/drop data indicating the relation between the lighting time and the temperature rise of the irradiation field lamp (collimator lamp) and the relation between the lighting-off time and the temperature drop of the collimator lamp. The pseudo temperature counter calculates the temperature of the current collimator lamp from the lighting time and the lighting-off time of the collimator lamp and the temperature rise/drop data stored in the storage unit. The lighting control unit prohibits the lighting of the collimator lamp when the temperature of the collimator lamp calculated by the pseudo temperature counter has exceeded and allows the lighting of the collimator when the temperature of the collimator calculated by the pseudo temperature counter has become equal to or less than the set temperature.

With the aforementioned configuration, it is possible to prevent that the temperature of the apparatus becomes equal to or higher than a certain level without increasing the production cost of the apparatus. Moreover, when the temperature of the apparatus has become equal to or lower than the certain level, it becomes possible to resume the X-ray image capturing.

There is also an X-ray image capturing apparatus capable of changing the set lighting time in accordance with the work time required by a user such as a technician (see, for example, Patent Document 2). Other than the above, there is an X-ray image capturing apparatus capable of controlling the lighting time according to the power consumption of the collimator lamp and the residual power of the battery in a mobile X-ray image capturing apparatus equipped with a battery (see, for example, Patent Document 3).

PRIOR ART

Patent Document

Patent Document 1: Japanese Unexamined Patent Application Publication No. 2012-55421
Patent Document 2: Japanese Unexamined Patent Application Publication No. 2013-183959
Patent Document 3: Japanese Unexamined Patent Application Publication No. 2005-304696

SUMMARY OF THE INVENTION

Problems to be Solved by the Invention

However, in the case of conventional techniques, even in cases where it is desired to continuously use the apparatus, when the lighting of the collimator lamp is prohibited due to the temperature limitation, there are such problems that the apparatus cannot be used and the irradiation field cannot be adjusted. As a result, there are problems of inconvenience that a user, such as a technician, cannot use the apparatus at the timing when the user wishes to use the apparatus, which makes a subject as a patient wait.

A conventional collimator lamp uses a halogen lamp with large heat generation (having power consumption of about 100 W) as described above. Therefore, it was necessary to prepare protection such as temperature restriction in consideration of the temperature of the device exterior, as described in the aforementioned Patent Document 1: Japanese Unexamined Patent Publication No. 2012-55421. Therefore, by using a light source with low power consumption such as a light emitting diode (LED: Light Emitting Diode), the same illuminance as that of a halogen lamp can be obtained with power consumption of about 10 W to 20 W. As a result, even if the light emitting diode (LED) is continuously lighted, the temperature of the device exterior does not become high in temperature, so it is not necessary to consider the exterior temperature.

As described above, in recent years, an X-ray image capturing apparatus equipped with a collimator lamp composed of an LED is used. On the other hand, when trying to use an X-ray image capturing apparatus having a collimator lamp composed of only an LED, it is necessary to prepare an entire apparatus. Furthermore, in the case of an LED, lighting is attained by a direct current, so an AC power source cannot be directly taken into and therefore it is required to prepare an AC/DC conversion board for converting an AC to a DC. Therefore, in order to enhance the general versatility, devices have been developed in which a configuration capable of controlling the lighting of both of a halogen lamp and an LED and selecting them have been developed.

When using such equipment, in addition to an AC/DC conversion board, it is sufficient to prepare only a control board connectable to both a halogen lamp and an LED and switchable to either one, or a halogen lamp control board (halogen lamp lighting circuit) for lighting a halogen lamp and an LED control board (LED lighting circuit) for lighting an LED. For this reason, existing equipment in the X-ray image capturing apparatus other than the AC/DC conversion board and control boards can be used. The AC/DC conversion board and the control boards are mounted in a device body.

In this way, when the light source connected to the device body is changed from a halogen lamp to an LED, the lighting control unit constituted by, e.g., a central processing unit (CPU) detects that the LED is connected, so that the lighting control unit can ignore the temperature limitation. However, there requires setting to inform the lighting control unit that the LED is connected.

Normally, these AC/DC conversion board and the control boards are mounted on a device body and shipped after assembling the device. Alternatively, at the time of the maintenance, these AC/DC conversion board and control boards are installed on the device body. Therefore, an assembler at the time of the shipment or a serviceman at the time of the maintenance manually performs settings to inform the lighting control unit that the LED is connected. In cases where a human such as an assembler at the time of the shipment or a service person at the time of the maintenance is manually set, it takes time to perform settings and there is a risk of incorrectly carrying out settings.

Especially, the risk of incorrectly carrying out settings will be specifically described. In cases where the halogen lamp setting has been made regardless that an LED is actually connected, the temperature limitation is applied as usual, which merely results in that it cannot be used continuously for a long time. On the contrary, however, in cases where an LED setting has been actually made regardless that a halogen lamp is actually connected, the limitation on overheating of the exterior temperature is disabled, which may cause overheating of the device exterior.

The present invention was made in view of such circumstances, and aims to provide a radiography apparatus capable of preventing a risk of incorrectly carrying out setting and automatically carrying out setting for switching light sources.

Means for Solving the Problems

In order to attain such an object, the present invention has the following configuration.

That is, the radiography apparatus (hereinafter referred to as "first invention") according to the present invention is a radiography apparatus equipped with a radiation irradiation means configured to irradiate radiation toward a subject. The radiography apparatus includes: a light source configured to illuminate an irradiation field of the radiation with visible light; a light source lighting control means configured to control lighting of the light source; a lighting time limitation means configured to limit a lighting time of the light source so as to be equal to or lower than a predetermined temperature; and a light source type discrimination means configured to discriminate a type of the light source connected to a device body, wherein the light source lighting control means changes the lighting time to be limited by the lighting time limitation means based on a result of discrimination by the light source type discrimination means.

According to the radiography apparatus (first invention) of the present invention, in addition to a light source for illuminating the irradiation field of radiation with visible light and a light source lighting control means for controlling the lighting of the light source, a lighting time limitation means for limiting a lighting time of the light source so as to be equal to or lower than a predetermined temperature and a light source type discrimination means for discriminating a type of the light source connected to a device body are provided. By limiting the lighting time of the light source by the lighting time limitation means so as to be equal to or lower than a predetermined temperature, overheating of the device exterior can be prevented. Based on the result of discrimination obtained by discriminating the type of the light source connected to the device body in the light source type discrimination means, the light source lighting control means changes the lighting time to be limited by the lighting time limitation means. As a result, it is not necessary for a person, such as, e.g., an assembler at the time of the shipment or a serviceman at the time of the maintenance, to manually carry out setting for switching light sources. The setting for switching light sources can be carried out automatically. Based on the result of the discrimination by the light source discrimination means, the lighting time limitation means changes the lighting time to be limited by the lighting time limitation means is changed. For this reason, a risk of incorrectly carrying out the setting can be prevented. For example, even if a light source with large heat generation (e.g., halogen lamp) is actually connected, the type of the light source is automatically discriminated as a connection target. Therefore, the lighting time is limited to be short, which in turn prevents overheating. On the other hand, even if a light source with small heat generation (e.g., LED) is actually connected, the type of the light source is automatically discriminated as a connection target. Therefore, the lighting time is set to be long to enable a consecutive long time use. Therefore, when there is a possibility of overheating of the exterior temperature due to the use of a light source with large heat generation, overheating can be prevented. In addition, when there is no possibility of overheating of the exterior temperature due to the use of a light source with small heat generation, consecutive long time use can be enabled. As a result, the risk of incorrectly carrying out the setting can be prevented, and the setting for switching light sources can be carried out automatically.

Further, a radiography apparatus (referred to as a "second invention") according to another invention, which is different from the first invention, is radiography apparatus equipped with a radiation irradiation means configured to irradiate radiation toward a subject. The radiography apparatus includes: a light source configured to illuminate an irradiation field of the radiation with visible light; a light source lighting control means configured to control lighting of the light source; a lighting time limitation means configured to limit a lighting time of the light source so as to be equal to or lower than a predetermined temperature; and a light source type discrimination means configured to discriminate a type of the light source connected to a device body, wherein the light source lighting control means disables the lighting time limitation means when the light source is discriminated as a semiconductor light source by a result of discrimination by the light source type discrimination means.

According to the radiography apparatus (second invention) of the present invention, in the same manner as in the first invention, in addition to a light source for illuminating an irradiation field of radiation with visible light and a light source lighting control means for controlling the lighting of the light source, a lighting time limitation means for limiting the lighting time of the light source so as to be equal to or lower than the predetermined temperature and a light source type discrimination means for discriminating the type of the light source connected to the device body are provided. By limiting the lighting time of the light source by the light time limitation means so as to be equal to or lower than the predetermined temperature, overheating of the device exterior can be prevented. Unlike the aforementioned first invention, in cases where the light source is discriminated as a semiconductor light source by the result of the discrimination obtained by discriminating the type of the light source connected to the device body with the light source type discrimination means, the light source lighting control means disables the lighting time limitation means. The semiconductor light source is composed of a semiconductor light source with small heat generation, such as, e.g., a laser diode (LD: Laser Diode) that emits phase-aligned visible light and the aforementioned LED. Therefore, in cases where a semiconductor light source with small heat generation is actually connected, the lighting time limitation means is disabled to set the lighting time to be longer, so that the light source can be used continuously for a long time. On the other hand, in cases where a light source with large heat generation other than a semiconductor light source (for example, halogen lamp) is actually connected, the lighting time limitation means is enabled to limit the lighting time to be short to prevent overheating. Therefore, in cases where there is no possibility of overheating of the exterior temperature by using a semiconductor light source with small heat generation, the lighting time limitation means is disabled, which enables to use the light source continuously for a long time. As a result, the risk of incorrectly carrying out the setting can be prevented, and the setting for switching light sources can be carried out automatically.

Further, a radiography apparatus (referred to as a "third invention") according to another invention, which is different from the first invention and the second invention, is a radiography apparatus equipped with a radiation irradiation means configured to irradiate radiation toward a subject. The radiography apparatus includes: a light source configured to illuminate an irradiation field of the radiation with visible light; a light source lighting control means configured to control lighting of the light source; a lighting power limitation means configured to limit lighting power of the light source so as to be equal to or lower than a predetermined temperature; and a light source type discrimination means configured to discriminate a type of the light source connected to a device body, wherein the light source lighting control means changes the lighting power to be limited by the lighting power limitation means based on a result of discrimination by the light source type discrimination means.

According to the radiography apparatus (third invention) of the present invention, in addition to a light source for illuminating an irradiation field of radiation with visible light and a light source lighting control means for controlling the lighting of the light source, a lighting power limitation means configured to limit lighting power of the light source so as to be equal to or lower than a predetermined temperature and a light source type discrimination means for discriminating a type of the light source connected to a device body are provided. By limiting the lighting power of the light source by the lighting power limitation means so as to be equal to lower than a predetermined temperature, overheating of the device exterior is prevented. Based on the result of the discrimination obtained by discriminating the type of the light source connected to the device body in the light source type discrimination means, the light source lighting control means changes the lighting power to be limited by the lighting power limitation means. As a result, it is not necessary for a person, such as, e.g., an assembler at the time of the shipment or a serviceman at the time of the maintenance to manually carry out the setting for switching light sources, and the setting for switching can be carried out automatically. Based on the result of discrimination obtained by discriminating the type of the light source connected to the device body by the light type discrimination means, the lighting power limitation means changes the lighting power to be limited by the lighting power limitation means. This prevents a risk of incorrectly carrying out the setting. For example, even if a light source with large heat generation (e.g., halogen lamp) is actually connected, the type of the light source is automatically discriminated as a connection target. Therefore, for example, after monitoring the lighting time with a timer, overheating is prevented by lowering the lighting power. On the other hand, even if a light source with small heat generation (e.g., LED) is actually connected, the type of the light source is automatically discriminated as a connection target. Therefore, for example, even after monitoring the lighting time with a timer, the lowering rate of the lighting power is set to be lower. Therefore, in cases where there is a possibility of overheating of the exterior temperature by using a light source with large heat generation, overheating is prevented. In cases where there is no possibility of overheating of the exterior temperature by using a light source with small heat generation, it is possible to carry out the setting so that the lowering rate of the lighting power is lowered. As a result, the risk of incorrectly carrying out the setting can be prevented, and the setting of switching light sources can be performed automatically.

A radiographic apparatus (referred to as a "fourth invention") according to another invention, which is different from the first invention to the third invention, is a radiography apparatus equipped with a radiation irradiation means for irradiating radiation toward a subject. The radiography apparatus includes: a light source configured to illuminate an irradiation field of radiation with visible light; a light source lighting control means configured to control lighting of the light source; a lighting power limitation means configured to limit lighting power of the light source so as to be equal to or lower than a predetermined temperature; and a light source type discrimination means configured to discriminate a type of the light source connected to a device body, wherein the light source lighting control means disables the lighting power limitation means when the light source is discriminated as a semiconductor light source by a result of discrimination by the light source type discrimination means.

According to the radiography apparatus (fourth invention) of the present invention, in the same manner as in the third invention, in addition to a light source for illuminating an irradiation field of the radiation with visible light and a light source lighting control means for controlling the lighting of the light source, a lighting power limitation means for limiting the lighting power of the light source so as to be equal to or lower than a predetermined temperature and a light source type discrimination means for discriminating a type of the light source connected to a device body are provided. By limiting the lighting power of the light source by the lighting power limitation means so as to be equal to or lower than a predetermined temperature, overheating of the device exterior is prevented. Unlike the aforementioned Embodiment 3, in cases where the light source is discriminated as a semiconductor light source by the result of the discrimination obtained by discriminating the type of the light source connected to the device body with the light source type discrimination means, the light source lighting control means disables the lighting power limitation means. As mentioned with respect to the second invention, the semiconductor light source is composed of a semiconductor light source with small heat generation, such as, e.g., an LD (laser diode) and the aforementioned LED. Therefore, in cases where a semiconductor light source with small heat generation is actually connected, by disabling the lighting power limitation means, the setting is carried out without lowering the lighting power or so that the lighting power is set to be large. On the other hand, in cases where a light source with large heat generation (for example, halogen lamp) other than a semiconductor light source is actually connected, by enabling the lighting power limitation means, the lighting power is lowered to thereby prevent overheating. Therefore, in cases where there is no possibility of overheating of the exterior temperature by using a semiconductor light source with small heat generation, by disabling the lighting power limitation means, it is possible to carrying out the setting without lowering the lighting power or so that the lighting power is set to be large. As a result, the risk of incorrectly carrying out the setting, and the setting for switching light sources can be carried out automatically.

An example of the discrimination of the type of the light source in the radiography apparatus (the first invention to the fourth invention) according to the aforementioned inventions is as follows.

That is, the light source type discrimination means detects that the light source is connected. In the case of this example, it is possible to discriminate the type of the light source by simply preparing one control board and connecting a light source to the control board mounted on the device body.

Another example of the discrimination of the type of light source in the radiography apparatus (the first invention to the fourth invention) according to the aforementioned inventions is as follows.

That is, the light source type discrimination means detects that the light source lighting control means is mounted on a control board dedicated to the light source for lighting the light source. In the case of this example, by simply preparing control boards dedicated to light sources (lighting circuits dedicated to light sources) by the number of types of light sources and mounting any one of the control boards on the device body to mount the same light source lighting control means (e.g., CPU) to the control board, it is possible to discriminate the type of the light source.

Effects of the Invention

According to the radiography apparatus (the first invention and the third invention) of the present invention, a lighting time/lighting power limitation means for limiting a lighting time/lighting power of the light source so as to be equal to or lower than a predetermined temperature and a light source type discrimination means for discriminating a type of the light source connected to a device body are provided. The light source lighting control means changes the lighting time/lighting power to be limited by the lighting time/lighting power limitation means based on the result of the discrimination by the light source type discrimination means. As a result, the risk of incorrectly carrying out the setting can be prevented, and the setting for switching light sources can be carried out automatically.

Further, according to the radiography apparatus (the second invention and the fourth invention) of the present invention, a lighting time/lighting power limitation means for limiting a lighting time/lighting power of the light source so as to be equal to or lower than a predetermined temperature and a light source type discrimination means for discriminating the type of the light source connected to a device body are provided. In cases where the light source is a semiconductor light source discriminated by the result of the discrimination by the light source type discrimination means, the light source lighting control means disables the lighting time/lighting power limitation means. As a result, the risk of incorrectly carrying out the setting, and the setting for switching light sources can be carried out automatically.

EMBODIMENT 1

Figure 1:
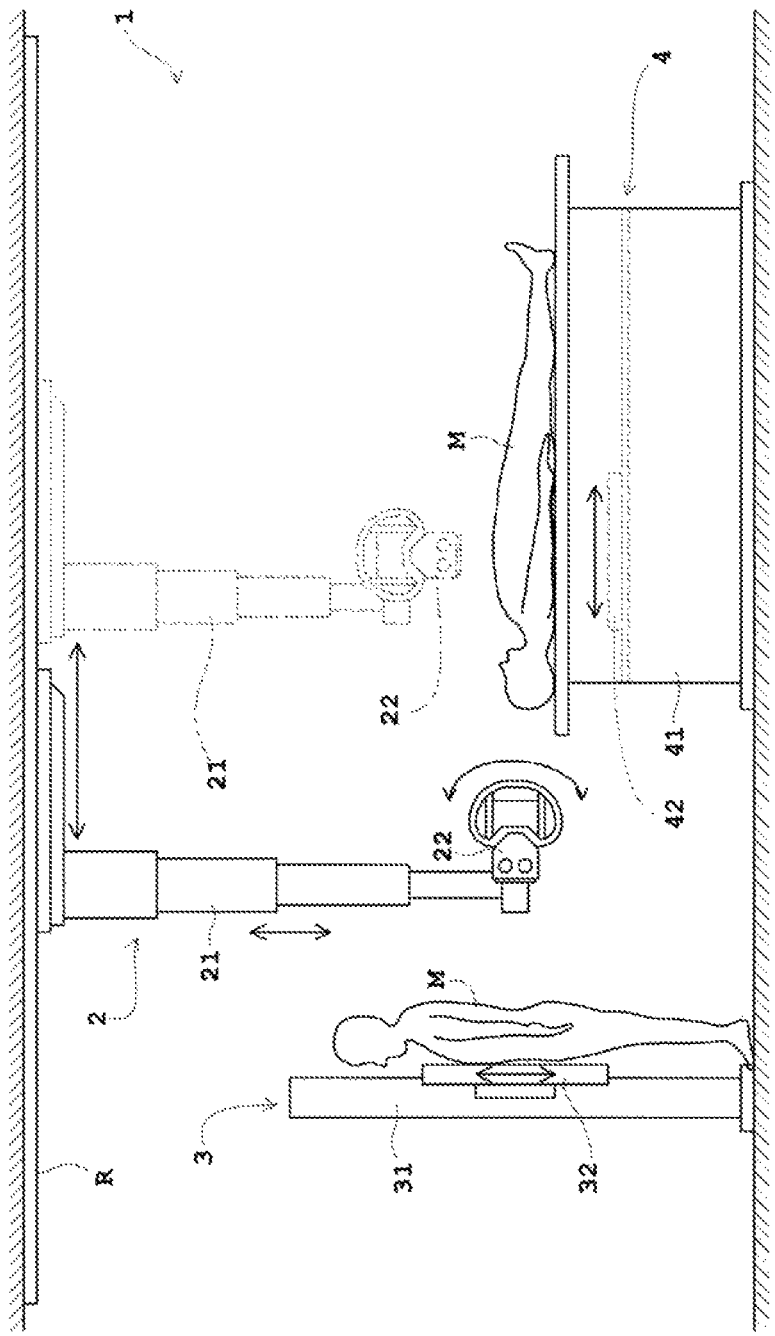
FIG. 1 is a schematic diagram of an X-ray image capturing apparatus according to each embodiment.
Figure 2:
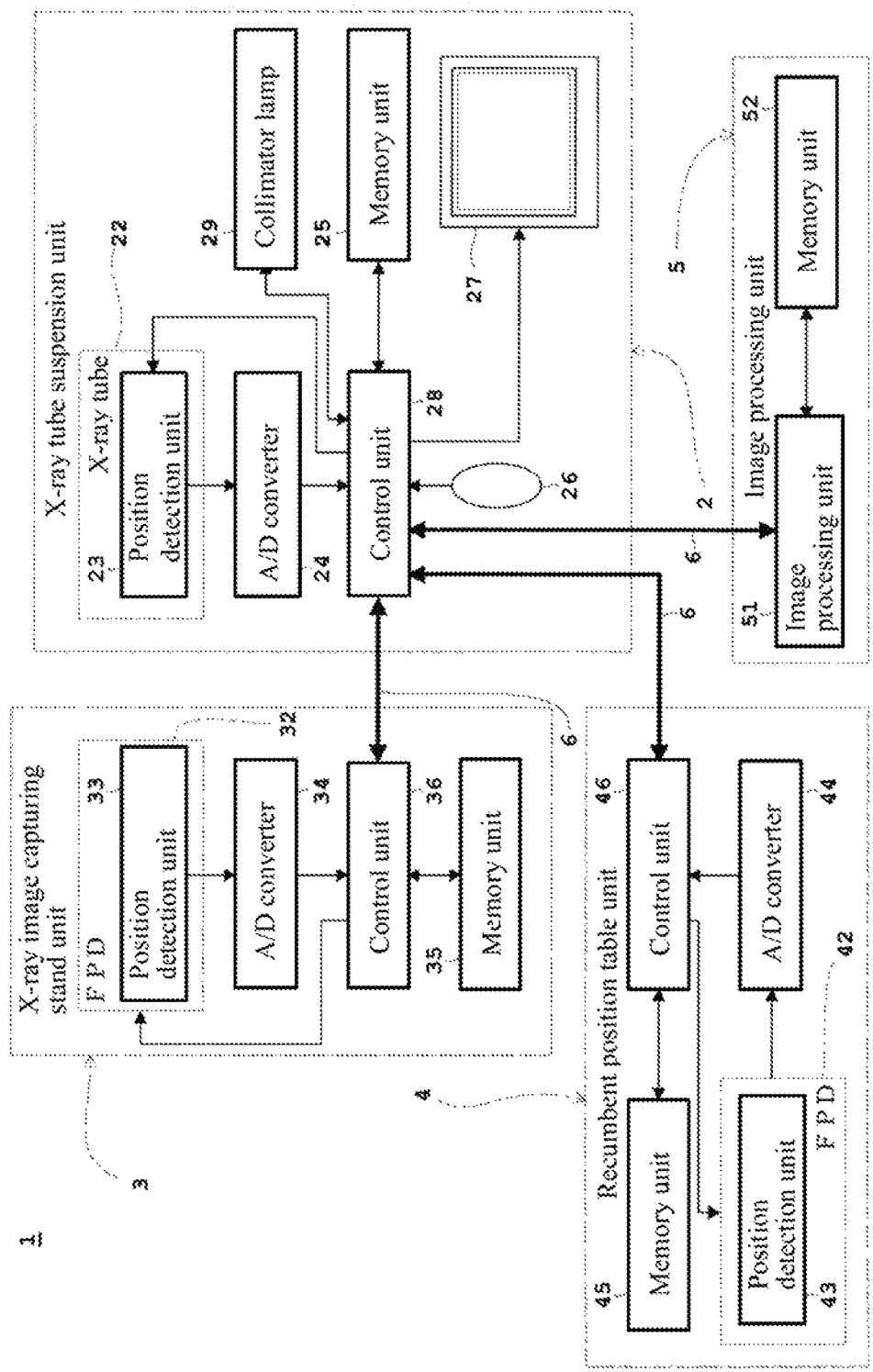
FIG. 2 is a block diagram of the X-ray image capturing apparatus according to each embodiment.
Figure 3:
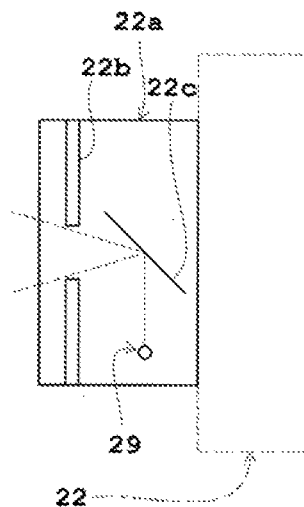
FIG. 3 is a schematic diagram when a collimator lamp is provided to an X-ray tube.

Hereinafter, Embodiment 1 of the present invention will be described with reference to the drawings. FIG. 1 is a schematic diagram of an X-ray image capturing apparatus according to each embodiment. FIG. 2 is a block diagram of the X-ray image capturing apparatus according to each embodiment. FIG. 3 is a schematic diagram when a collimator lamp is provided to the X-ray tube. Including Embodiments 2 to 5 which will be described later, in Embodiment 1, the following descriptions will be made by exemplifying an X-ray as radiation and also by exemplifying an X-ray image capturing apparatus that performs X-ray image capturing as a radiography apparatus.

Including Embodiments 2 to 5 which will be described later, as shown in FIG. 1, the X-ray image capturing apparatus 1 according to Embodiment 1 is provided with an X-ray tube suspension unit 2 configured to suspensively support the X-ray tube 22 so as to be movable along the ceiling, an X-ray image capturing stand unit 3 configured to perform X-ray image capturing of a subject M in a standing posture state, a recumbent position table unit 4 configured to perform X-ray image capturing of a subject M in a recumbent posture state, and an image processing unit 5 (not shown in FIG. 1) configured to perform image processing of an X-ray image of the subject M. As shown in FIG. 2, the X-ray tube suspension unit 2, the X-ray image capturing stand unit 3, the recumbent position table unit 4, and the image processing unit 5 are electrically connected to each other by communication cables 6. With the communication cables 6, the X-ray tube suspension unit 2, the X-ray image capturing stand unit 3, the recumbent position table unit 4, and the image processing unit 5 are configured in a mutually communicable manner.

As shown in FIG. 1, the X-ray tube suspension unit 2 is provided with a support post 21 capable of moving along the ceiling and vertically expandable and retractable, and an X-ray tube 22 supported by the support post 21 in a direction adjustable manner. As shown in FIG. 2, the X-ray tube suspension unit 2 is equipped with a position detection unit 23 for detecting the position and the angle of the X-ray tube 22 and an A/D converter 24 for converting an analog voltage of the position information obtained by the position detection unit 23 into digital data. Other than the above, the X-ray tube suspension unit 2 is equipped with a memory unit 25, an input unit 26, an output unit 27, a control unit 28, and an irradiation field lamp (collimator lamp) 29. The specific structure of the control unit 28 and the collimator lamp 29 will be described later. The X-ray tube 22 corresponds to the radiation irradiation means in the present invention. The control unit 28 corresponds to the light source lighting control means, the lighting time limitation means, and the light source type discrimination means in the present invention. The irradiation field lamp (collimator lamp) 29 corresponds to the light source in the present invention.

As shown in FIG. 1, the X-ray image capturing stand unit 3 is equipped with an upright stand 31 for supporting a subject M in a standing posture and a flat panel type X-ray detector (FPD) 32 mounted on the upright stand 31 in a vertically movable manner. As shown in FIG. 2, the X-ray image capturing stand unit 3 is equipped with a position detection unit 33 for detecting the position of the FPD 32 and an A/D converter 34 for converting the analog voltage of the position information obtained by the position detection unit 33 into digital data. Other than the above, the X-ray image capturing stand unit 3 is equipped with a memory unit 35 and a control unit 36. In the same manner as in the X-ray tube suspension unit 2, the X-ray image capturing stand unit 3 may be equipped with an input unit and an output unit. Further, the control unit 28 of the X-ray tube suspension unit 2 may directly control the FPD 32 of the X-ray image capturing stand unit 3 without providing the memory unit 35 and the control unit 36 in the X-ray image capturing stand unit 3.

As shown in FIG. 1, the recumbent position table unit 4 is provided with a recumbent position table 41 for placing a subject M in a recumbent posture and a flat panel type X-ray detector (FPD) 42 mounted on the recumbent position table 41 in a horizontally movable manner. As shown in FIG. 2, the recumbent position table unit 4 is equipped with a position detection unit 43 for detecting the position of the FPD 42 and an A/D converter 44 for converting the analog voltage of the position information obtained by the position detection unit 43 into digital data. Other than the above, the recumbent position table unit 4 is equipped with a memory unit 45 and a control unit 46. In the same manner as in the X-ray tube suspension unit 2, the recumbent position table unit 4 may be equipped with an input unit and an output unit. Further, the control unit 28 of the X-ray tube suspension unit 2 may directly control the FPD 42 of the recumbent position table unit 4 without equipping the memory unit 45 and the control unit 46 in the recumbent position table unit 4.

As shown in FIG. 2, the image processing unit 5 is equipped with an image processing unit 51 for creating an X-ray image (X-ray captured image) by performing image processing based on the X-ray output signal obtained by the FPD 32 of the X-ray image capturing stand unit 3 or the FPD 42 of the recumbent position table unit 4. Other than the above, the image processing unit 5 is equipped with a memory unit 52 that writes and stores an X-ray image. In the same manner as in the X-ray tube suspension unit 2, the image processing unit 5 may be equipped with an input unit and an output unit. Further, it may be configured such that an X-ray image is written and stored in the memory unit 25 of the X-ray tube suspension unit 2 without equipping the memory unit 52 in the image processing unit 5.

The support post 21 of the X-ray tube suspension unit 2 is configured to be movable along the rail R mounted along the ceiling. The rail R is also mounted along the depth direction of the paper of FIG. 1, so that the support post 21 is movable along the depth direction. This support post 21 is configured to be extendable and contractible. The X-ray tube 22 is supported by the support post 21, so that the X-ray tube 22 can be moved horizontally/vertically. Further, the orientation of the X-ray tube 22 is adjustable. Accordingly, it is possible to perform X-ray image capturing in a standing posture by adjusting the orientation of the X-ray tube 22 by moving horizontally/vertically as shown by the two-dot chain line in FIG. 1 toward the upright stand 31 of the X-ray image capturing stand unit 3. Furthermore, it is possible to perform X-ray image capturing in a recumbent posture by adjusting the direction of the X-ray tube 22 by moving the X-ray tube 22 horizontally/vertically upward and downward as shown by the two-dot chain line in FIG. 1 toward the recumbent position table 41 of the recumbent position table unit 4.

As shown in FIG. 2, a position detection unit 23 is provided in the X-ray tube 22, and the position and the angle of the X-ray tube 22 are detected by the position detection unit 23. The position detection unit 23 is configured by, for example, a potentiometer, and the resistance value of the potentiometer changes as the X-ray tube 22 moves or rotates, and the output voltage changes with respect to the reference voltage according to the resistance value. This output voltage is an analog voltage, and the analog voltage of the positional information (including the angle) obtained by the potentiometer is sent to the A/D converter 24. The A/D converter 24 converts the analog voltage into digital data.

The memory unit 25 of the X-ray tube suspension unit 2 writes and stores the X-ray image acquisition area for each image capturing and the image capturing position in each image capturing via the control unit 28, and reads it as necessary. The memory unit 25 of the X-ray tube suspension unit 2, the memory unit 35 of the X-ray image capturing stand unit 3, the memory unit 45 of the recumbent position table unit 4, and the memory unit 52 of the image processing unit 5 are each configured by a storage medium represented by, e.g., a ROM (Read-only Memory) and a RAM (Random-Access Memory).

The input unit 26 of the X-ray tube suspension unit 2 sends data and instructions entered by an operator to the control unit 28. The input unit 26 is configured by a pointing device represented by a mouse, a keyboard, a joystick, a trackball, and a touch panel. In Embodiment 1, by pressing a lighting button (not shown), the collimator lamp 29 is lighted for a predetermined time, and when the predetermined time has elapsed, the collimator lamp 29 automatically turns off.

The output unit 27 of the X-ray tube suspension unit 2 is configured by, e.g., a display unit represented by a monitor or a printer. In cases where the output unit 27 is a display unit, the output is displayed, and in cases where the output unit 27 is a printer, the output is printed. Further, the output unit 27 may be configured by a touch panel on which the aforementioned lighting button is mounted, and this touch panel may be attached to the X-ray tube 22. In this way, the function of the input unit 26 may be provided in the output unit 27.

The control unit 28 of the X-ray tube suspension unit 2 totally controls each part constituting the X-ray tube suspension unit 2. The control unit 28 of the X-ray tube suspension unit 2, the control unit 36 of the X-ray image capturing stand unit 3, the control unit 46 of the recumbent position table unit 4, and the image processing unit 51 of the image processing unit 5 are configured by a control board on which a central processing unit (CPU), etc., is mounted. Including Embodiments 2 to 5 which will be described later, in Embodiment 1, the control unit 28 has the function of the light source lighting control means for controlling the lighting of the collimator lamp 29 and the function of the light source type discrimination means for discriminating the type of the collimator lamp 29 connected to the device body. In addition, including Embodiment 2 which will be described later, in Example 1, the control unit 28 has a function of the lighting time limitation means for limiting the lighting time of the collimator lamp 29 so that it becomes equal to or lower than the predetermined temperature and a function for changing the lighting time to be limited by the lighting time limitation means based on the result of the discrimination by the function of the light source type discrimination means.

The collimator lamp 29 of the X-ray tube suspension unit 2 is built in the collimator (X-ray diaphragm) 22a for controlling the irradiation field of the X-ray from the X-ray tube 22 as shown in FIG. 3. Specifically, leaves 22b capable of changing its irradiation field size and a reflection mirror 22c are provided, and it is configured to reflect the visible light (light) irradiated from the collimator lamp 29 by the reflection mirror 22c to pass through the leaves 22b. By operating the leaves 22b of the collimator 22a, it is possible to freely set the size of the irradiation field (also called "lighting field") irradiated from the collimator lamp 29. In this way, the collimator lamp 29 illuminates the entire irradiation field adjusted by the leaves 22b of the collimator 22a with visible light. Including Embodiments 2 to 5 which will be described later, in Embodiment 1, the collimator lamp 29 is composed of a halogen lamp or a light emitting diode (LED) and is configured to be switched to either one.

As shown in FIG. 1, the upright stand 31 of the X-ray image capturing stand unit 3 is installed on the floor surface. The FPD 32 of the X-ray image capturing stand unit 3 is capable of moving upward and downward along the upright stand 31. On the other hand, the recumbent position table 41 of the recumbent position table unit 4 is also installed on the floor surface. The FPD 42 of the recumbent position table unit 4 is capable of horizontally moving within the recumbent position table 41.

As shown in FIG. 2, the position detection unit 33 is provided in the FPD 32 of the X-ray image capturing stand unit 3, so that the position detection unit 33 detects the position of the FPD 32. On the other hand, the position detection unit 43 is also provided in the FPD 42 of the recumbent position table unit 4, so that the position detection unit 43 detects the position of the FPD 42. In the same manner as in the position detection unit 23 of the X-ray tube suspension unit 2, the position detection unit 33 of the X-ray image capturing stand unit 3 and the position detection unit 43 of the recumbent position table unit 4 each are also composed of a potentiometer, the resistance value of the potentiometer changes in accordance with the movement of the FPDs 32 and 42, so that the output voltage changes with respect to the reference voltage in accordance with the resistance value. This output voltage is an analog voltage, and the analog voltage of the positional information obtained by the potentiometer is sent to the A/D converter 34 in the case of the X-ray image capturing stand unit 3, and is sent to the A/D converter 44 in the case of the recumbent position table unit 4. The A/D converters 34 and 44 convert the analog voltage into respective digital data. Further, the analog voltage of the positional information obtained by the potentiometer of the X-ray image capturing stand unit 3 and the recumbent position table unit 4 is also sent to the X-ray tube suspension unit 2 via the communication cables 6.

The memory unit 35 of the X-ray image capturing stand unit 3 writes and stores the upper end position and the lower end position of the FPD 32 in the X-ray image capturing and reads it out as necessary. On the other hand, the memory unit 45 of the recumbent position table unit 4 writes and stores the left end position and the right end position of the FPD 42 in the X-ray image capturing and reads it out as necessary.

The control unit 36 of the X-ray image capturing stand unit 3 totally controls each part constituting the X-ray image capturing stand unit 3, and the control unit 46 of the recumbent position table unit 4 totally controls each part constituting the recumbent position table unit 4.

The control unit 28 of the X-ray tube suspension unit 2 and the control unit 36 of the X-ray image capturing stand unit 3 are electrically connected by a communication cable 6. The control unit 28 of the X-ray tube suspension unit 2 and the control unit 46 of the recumbent position table unit 4 are electrically connected by a communication cable 6. The control unit 28 of the X-ray tube suspension unit 2 and the image processing unit 51 of the image processing unit 5 are electrically connected by a communication cable 6. By connecting as described above, the X-ray tube suspension unit 2, the X-ray image capturing stand unit 3, the recumbent position table unit 4, and the image processing unit 5 are configured to be able to communicate with each other. Other than the above, each control unit 28, 36, and 46 drivingly controls the X-ray tube 22 and the FPD 32 and 42, and each control unit 28, 36, and 46 controls a motor (not shown), thereby driving the motor of the X-ray tube 22 and the FPD 32 and 42. By driving the motor, it is possible to control the X-ray tube 22 and the FPD 32 and 42 so as to be positioned at a desired position and adjust the orientation of the X-ray tube 22 at a desired angle.

Figure 4:
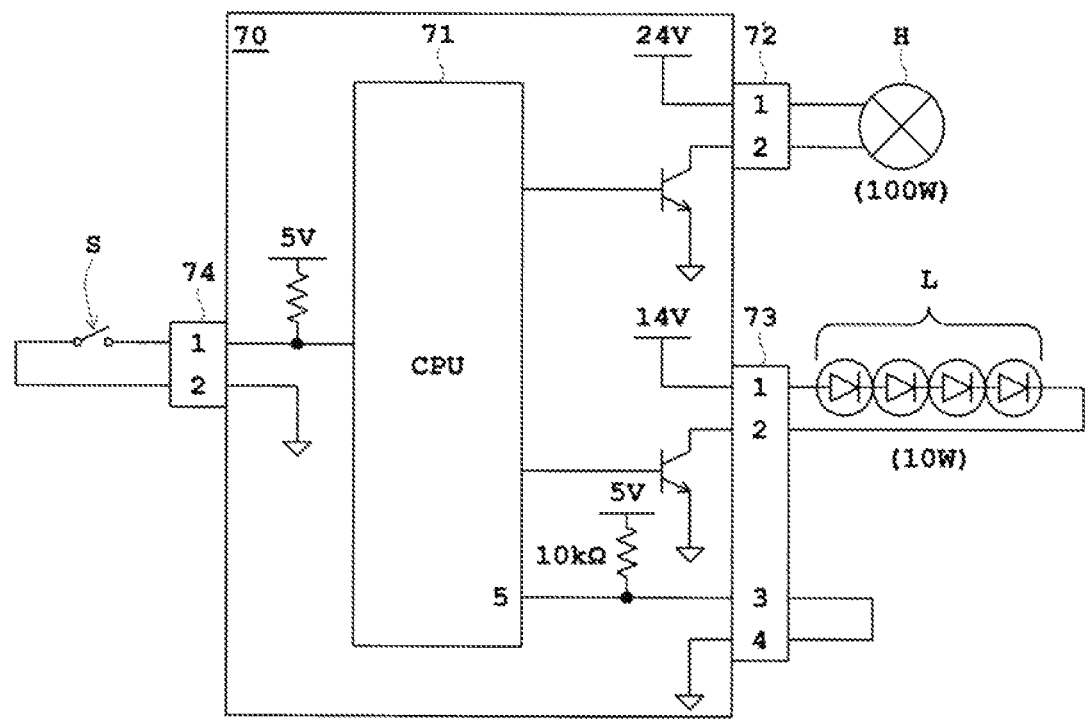
FIG. 4 is a control board and peripheral circuits according to Embodiment 1 for explaining a light source type discrimination means.

Next, a specific structure of the control unit 28 and a specific control by the control unit 28 according to Embodiment 1 will be described with reference to FIG. 4. FIG. 4 illustrates a control board and peripheral circuits according to Embodiment 1 for explaining a light source type discrimination means.

As shown in FIG. 4, the control unit 28 (see FIG. 2) is composed of a control board 70 having a function of a light source type discrimination means and is configured by mounting a central processing unit (CPU) 71 having a function of a light source lighting control means and a function of a lighting time limitation means on the control board 70. In this Embodiment 1, as shown in FIG. 4, one control board 70 is configured so as to be connectable to both the halogen lamp H and the light emitting diode (LED) L and switch to either one. In FIG. 4, the CPU 71 is exclusively used for the function of the light source lighting control means, and includes a built-in function of the lighting time limitation means.

Specifically, the control board 70 is mounted on the main body of the device (X-ray image capturing apparatus 1 in FIG. 1 and FIG. 2). As shown in FIG. 2, the control board 70 is electrically connected to each part constituting the X-ray image capturing apparatus 1 as the control unit 28.

As shown in FIG. 4, the control board 70 is electrically connected to the halogen lamp H via the halogen lamp connector 72, and is electrically connected to the light emitting diode (LED) L via the LED connector 73. The control board 70 is electrically connected to a lamp lighting switch S via a switch connector 74. The halogen lamp connector 72 and the switch connector 74 each have two pins (connection terminals), and the LED connector 73 has four pins (connection terminals).

No. 1 pin (denoted as "1" in FIG. 4) and No. 2 pin (denoted as "2" in FIG. 4) of the halogen lamp connector 72 are connected to the halogen lamp H. By inserting the halogen lamp connector 72 into the control board 70, the No. 1 pin is electrically connected to the DC power supply of 24 V, and the No. 2 pin is electrically connected to the CPU 71 via the transistor. Further, a DC power supply of 24 V is electrically connected to an AC/DC conversion board (not shown). After converting an alternating voltage into a DC voltage of 24 V, a power is supplied to the halogen lamp H. In the case of a halogen lamp H, it is also possible to light the lamp by an alternating current, so an AC power may be directly supplied thereto.

The No. 1 pin (denoted as "1" in FIG. 4) and the No. 2 pin (denoted as "2" in FIG. 4) of the switch connector 74 are connected to a lamp lighting switch S. By inserting the switch connector 74 into the control board 70, the No. 1 pin is electrically connected to a resistor connected to a DC power supply of 5 V in the middle and is electrically connected to the CPU 71. Further, No. 2 pin is grounded.

The No. 1 pin (denoted as "1" in FIG. 4) and the No. 2 pin (denoted as "2" in FIG. 4) of the LED connector 73 are connected to the light emitting diode (LED) L. By inserting the LED connector 73 into the control board 70, the No. 1 pin is electrically connected to the DC power supply of 14 V, and the No. 2 pin is electrically connected to the CPU 71 via the transistor. Further, a DC power supply of 14 V is electrically connected to an AC/DC conversion board (not shown). After converting an alternating voltage into a DC voltage of 14 V, a power is supplied to the light emitting diode (LED) L.

It is configured such that No. 3 pin (denoted by "3" in FIG. 4) and No. 4 pin (denoted by "4" in FIG. 4) of the LED connector 73 are short-circuited by a cable. By inserting the LED connector 73 into the control board 70, the No. 3 pin is electrically connected to a high resistance (for example, 10 kΩ) in the middle and connected to a DC power supply of 5 V and electrically connected to a No. 5 pin (denoted by "5" in FIG. 4) of the CPU 71. Note that the No. 4 pin is grounded.

The No. 5 pin of the CPU 71 becomes a high logic state when the voltage is 3.7 V to 5 V and becomes a low logic state when the voltage is 0 V to 0.7 V. The reasons that the threshold value margin is given to the voltage for detecting the logic state are to consider a voltage drop and noise in the case of the high logic state and to consider noise in the case of the low logic state. By giving the threshold value margin to the voltage for detecting the logic state, even if a voltage drop or noise is present in the case of the high logic state, it is possible to set within the range of 3.7 V to 5 V, and even if there is noise in the case of the low logic state, it is possible to set within the range of 0 V to 0.7 V. Therefore, even if there is a voltage drop and/or noise, false detection can be prevented. As for the threshold value range of the voltage for detecting the logic state, it is not limited within the range described above (the voltage for detecting the high logic state is in the range of 3.7 V to 5 V, the voltage for detecting the low logic state is in the range of 0 V to 0.7 V).

When a halogen lamp H is connected to the control board 70 and the light emitting diode (LED) L is not connected, since the LED connector 73 connected to the light emitting diode (LED) L is not inserted into the control board 70, the No. 5 pin of the CPU 71 is pulled up to almost 5 V by the 5 V DC power supply connected in the middle and becomes a high logic state. Although a certain voltage drop occurs due to the resistance connected to the DC power supply of 5 V, since the resistance is high resistance of, for example, about 10 kΩ, the current flowing through the resistor is on the order of micro ampere (μA), which can be ignored. In this way, when the light source connected to the control board 70 is a halogen lamp H, it is detected that the No. 5 pin of the CPU 71 has reached the high logic state. As a result, it is detected that the light source connected to the control board 70 is a halogen lamp H, which in turn automatically discriminates that the type of the detected light source is a halogen lamp H.

To the contrary, in the case of not connecting a halogen lamp H to the control board 70 and connecting a light emitting diode (LED) L, when the LED connector 73 leading to the light emitting diode (LED) L is inserted into the control board 70, the No. 3 pin and the No. 4 pin are short-circuited by the cable attached to the LED connector 73. As a result, the No. 5 pin of the CPU 71 drops to the low logic state due to the grounded No. 4 pin. As described above, in cases where the light source connected to the control board 70 is a light emitting diode (LED) L, it is detected that the No. 5 pin of the CPU 71 has reached the low logic state. As a result, it is detected that the light source connected to the control board 70 is the light emitting diode (LED) L, which in turn automatically discriminates that the type of the detected light source is the light emitting diode (LED) L.

Next, a specific control by the control unit 28 according to Embodiment 1 will be described. As for the concrete control method for limiting the lighting time of the light source by the control unit 28, for example, the following control method 1 to control method 4 can be exemplified.

[Control Method 1]

As described in Patent Document 1: Japanese Unexamined Patent Application Publication No. 2012-55421, the temperature rise and the temperature drop are counted up or counted down as a pseudo temperature counter, and when the count value exceeds a set value, the lighting of the collimator lamp is stopped to prevent the exterior temperature from reaching a high temperature.

When a halogen lamp is used, for example, the count value is counted up by 2 per second during the lighting, and is counted down by 1 per second while the lamp is in a lighting-off state. That is, when the halogen lamp is lighted off in a time twice the lighting time, the count value before lighting is maintained. When the count value is counted down to "0", the count value will not be further counted down so as to become minus and the count value "0" is maintained. When the count value reaches, for example, 600, lighting is stopped.

In the aforementioned example, as long as the lighting time and the lighting-off time of the halogen lamp are maintained at 1:2, there does not occur that protection such as temperature limitation does not work, so that the collimator lamp will not be forcibly lighted off. Conversely, for example, when the lamp is continuously lighted for 5 minutes (=300 seconds), the count value reaches 600, i.e., 2 counts/second×300 seconds=600, which activates the protection. As a result, the collimator lamp is forcibly lighted off.

This is an example of a calculation when the gradient of the temperature rise is twice sharper than the gradient of the temperature drop in the case of using a halogen lamp. Hereinafter, in this specification, the control method according to this calculation is called "control method 1". In the case of using an LED, the lighting time to be limited by a lighting time limitation means by the control method 1 is changed as follows.

For example, in the case of a halogen lamp, lighting was prohibited when the count reaches 600 counts, but, in the case of an LED, lighting is prohibited when the count value reaches 1,200. Alternatively, in the case of a halogen lamp, the count value was counted up by 2 per second, but in the case of an LED, the count value is counted up by 1 per second.

The control method 1 as described in Patent Document 1: Japanese Unexamined Patent Application Publication No. 2012-55421 is complicated in calculation and control, but can be realized by a CPU. In place of a control method like the control method 1 which is complicated in calculation and control, for example, the following simple control methods 2 to 4 may be used.

[Control Method 2]

In cases where a halogen lamp is used, for example, when lighting is continued for 5 minutes, lighting is prohibited for 10 minutes thereafter with the temperature limitation. Hereinafter, in this specification, this control method is referred to as "control method 2". In the case of using an LED, the lighting time to be limited by a lighting time limitation means by the control method 2 is changed as follows.

For example, in the case of a halogen lamp, the temperature limitation was applied after the consecutive 5-minute lighting. However, in the case of an LED, after the consecutive 10-minute lighting, the temperature limitation is applied.

[Control Method 3]

In the case of using a halogen lamp, for example, when lighting is continued for 5 minutes, lighting is prohibited until the device is reactivated with a temperature limitation thereafter. In other words, when the device is restarted after consecutive 5-minute lighting, protection such as a temperature limitation will be released. Therefore, in cases where the slope of the temperature rise is twice sharper than the slope of the temperature drop, users, such as, e.g., technicians, should be careful so as not to reactivate the device within 10 minutes immediately after applying the temperature limitation. Hereinafter, in this specification, this control method is referred to as "control method 3". In the case of using an LED, the lighting time to be limited by a lighting time limitation means by the control method 3 is changed as follows.

For example, in the case of a halogen lamp, the temperature limitation was applied after the consecutive 5-minute lighting, but in the same manner as the control method 2, in the case of an LED, the temperature limitation is applied after the consecutive 10-minute lighting.

[Control Method 4]

In the case of using a halogen lamp, the lamp lights for, e.g., 30 seconds by pressing the lighting button (not shown) once. By pressing the lighting button 10 times, the lighting time becomes 30 seconds/time×10 times=300 seconds, so the lamp lights consecutively for 5 minutes (=300 seconds). For the 10 minutes after the consecutive 5-minute lighting, a temperature limitation is applied so that the lamp lights only for 10 seconds with one press of the lighting button. Hereinafter, in this specification, this control method is referred to as "control method 4". In the case of using an LED, the lighting time to be limited by a lighting time limitation means by the control method 4 is changed as follows.

For example, in a halogen lamp, a temperature limitation was applied so that the lamp lights for only 10 seconds by pressing the lighting button once for 10 minutes after the consecutive 5-minute lighting. However, in an LED, for 10 minutes after the consecutive 5-minute lighting, a temperature limitation is applied so that the lamp lights for up to 25 seconds by pressing the lighting button one.

According to the X-ray image capturing apparatus 1 of Embodiment 1 having the aforementioned configuration, in addition to the light source (collimator lamp 29 in each embodiment) for irradiating visible light (light) to an irradiation field of radiation (X-ray in each embodiment) and a light source lighting control means (CPU 71 in FIG. 4) for controlling the lighting of the light source (collimator lamp 29), a lighting time limitation means (built in the CPU 71 in FIG. 4) for limiting the lighting time of the light source (collimator lamp 29) so as to be equal to or lower than the predetermined temperature and a light source type discrimination means (control board 70 in FIG. 4) for discriminating the type of the light source connected to the device body are provided. The lighting time limitation means (built in the CPU 71) limits the lighting time of the light source (collimator lamp 29) so that the temperature of the device exterior becomes equal to or lower than a predetermined temperature, thereby preventing overheating of the device exterior. Based on the result of the discrimination obtained by discriminating the type of the light source connected to the device body in the light source type discrimination means (control board 70), the lighting time is changed by the lighting time limitation means (built in the CPU 71). As a result, it is not necessary for a person, such as, e.g., a shipping assembler at the time of the shipment or a serviceman at the time of the maintenance to manually carry out setting for switching light sources (collimator lamp 29), and the switching can be set automatically. Further, based on the result of discrimination by the light source type discrimination means (control board 70), the lighting time which is limited by the lighting time limitation means (built in the CPU 71) is changed. This prevents a risk of incorrectly carrying out the setting. For example, even if a light source with large heat generation (e.g., halogen lamp) is actually connected, the type of the light source is automatically discriminated as a connection target. Therefore, the lighting time is shortened, which in turn prevents overheating. On the other hand, even if a light source with small heat generation (e.g., LED) is actually connected, the type of the light source is automatically discriminated as a connection target. Therefore, the lighting time is set to be long, which in turn enables a consecutive long time use. Therefore, when there is a possibility of overheating of the exterior temperature due to the use of a light source with large heat generation, overheating can be prevented. In addition, when there is no possibility of overheating of the exterior temperature due to the use of a light source with small heat generation, consecutive long time use can be made. As a result, the risk of incorrectly carrying out the setting, and the automatic setting for switching light sources can be carried out.

In this Embodiment 1, the light source type discrimination means detects the connection of the light source. As shown in FIG. 4, a light source (halogen lamp H or light emitting diode (LED) L) connected to the control board 70 is detected (in FIG. 4, the No. 5 pin of the CPU 71 is in a high logic state or in a low logic state), thereby discriminating the type of the detected light source. In the case of Embodiment 1, it is possible to discriminate the type of the light source by simply preparing one control board and connecting a light source to the control board mounted on the device body.

EMBODIMENT 2

Figure 5:
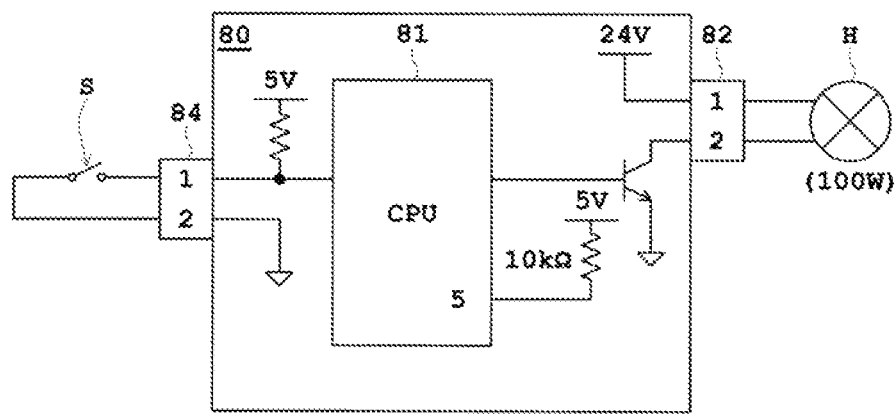
FIG. 5 is a halogen lamp control board (halogen lamp lighting circuit) and peripheral circuits according to Embodiment 2 for explaining a light source type discrimination means.
Figure 6:
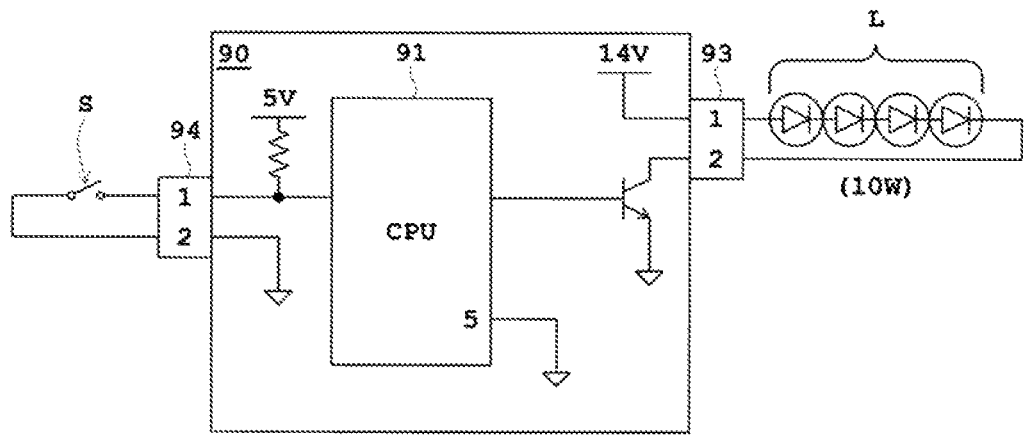
FIG. 6 is an LED control board (LED lighting circuit) and peripheral circuits according to Embodiment 2 for explaining a light source type discrimination means.

Hereinafter, Embodiment 2 of the present invention will be described with reference to the drawings. FIG. 5 is a halogen lamp control board (halogen lamp lighting circuit) and peripheral circuits according to Embodiment 2 for explaining a light source type discrimination means. FIG. 6 is an LED control circuit (LED lighting circuit) and peripheral circuits according to Embodiment 2 for explaining a light source type discrimination means. In Embodiment 2, X-ray image capturing is performed using the X-ray image capturing apparatus 1 shown in FIG. 1 which is the same as the aforementioned Embodiment 1, which will also be applied to the block diagram of FIG. 2.

In the aforementioned Embodiment 1, the light source type discrimination means is composed of the control board 70 as shown in FIG. 4. In this Embodiment 2, a control board (halogen lamp control board) for lightening a halogen lamp and a control board (LED control board) for turning on an LED are provided separately. Each of the boards includes the same CPU (light source lighting control means) mounted thereon.

Specifically, one of the halogen lamp control board (halogen lamp lighting circuit) 80 shown in FIG. 5 or the LED control board (LED lighting circuit) 90 shown in FIG. 6 is mounted on the apparatus (X-ray image capturing apparatus 1 in FIG. 1 and FIG. 2). The control board mounted on the device body is electrically connected to each part constituting the X-ray image capturing apparatus 1 as the control unit 28 as shown in FIG. 2.

First, the halogen lamp control board 80 will be described with reference to FIG. 5. As shown in FIG. 5, the control unit 28 (see FIG. 2) is composed of a halogen lamp control board 80 having a function of a light source type discrimination means, and a central processing unit (CPU) 81 having a function of a light source lighting control means and a function of a lighting time limitation means is provided on the halogen lamp control board 80. In Embodiment 2, as shown in FIG. 5, the halogen lamp control board 80 is electrically connected only to a halogen lamp H.

Specifically, the halogen lamp control board 80 is electrically connected to a halogen lamp H via the halogen lamp connector 82. Further, the halogen lamp control board 80 is electrically connected to a lamp lighting switch S via a switch connector 84. The halogen lamp connector 82 and the switch connector 84 each have two pins (connection terminals).

No. 1 pin (denoted as "1" in FIG. 5) and No. 2 pin (denoted as "2" in FIG. 5) of the halogen lamp connector 82 are connected to a halogen lamp H. Unlike the aforementioned Embodiment 1, the halogen lamp control board 80 is electrically connected only to the halogen lamp H. When the halogen lamp connector 82 is inserted into the halogen lamp control board 80, the No. 1 pin is electrically connected to the DC power supply of 24 V, and the No. 2 pin is electrically connected to the CPU 81 via the transistor.

No. 1 pin (denoted as "1" in FIG. 5) and No. 2 pin (denoted as "2" in FIG. 5) of the switch connector 84 are connected to a lamp lighting switch S. In the same manner as in the aforementioned Embodiment 1, when the switch connector 84 is inserted into the halogen lamp control board 80, the No. 1 pin is electrically connected to a resistor connected to the DC power supply of 5 V in the middle and is electrically connected to the CPU 81. Note that the No. 2 pin is grounded.

The No. 5 pin (denoted as "5" in FIG. 5) of the CPU 81 is electrically connected to a high resistance (for example, 10 kΩ) connected to a DC power supply of 5 V. When the CPU 81 is mounted on the halogen lamp control board 80, the No. 5 pin of the CPU 81 is pulled up to approximately 5 V by the DC power supply of 5 V and becomes a high logic state. As described above, although a certain voltage drop occurs due to the resistance connected to the DC power supply of 5 V, since the resistance is high resistance of, for example, about 10 kΩ, the current flowing through the resistor is on the order of micro ampere (μA), which can be ignored. In this way, when the CPU 81 is mounted on the halogen lamp control board 80, by detecting that the No. 5 pin of the CPU 81 has become the high logic state, it is detected that the CPU 81 is mounted on the halogen lamp control board 80, and it is automatically discriminated that the type of the detected light source is a halogen lamp H.

Next, an LED control board (LED lighting circuit) 90 will be described with reference to FIG. 6. As shown in FIG. 6, the control unit 28 (see FIG. 2) is composed of an LED control board 90 having a function of a light source type discrimination means, and a central processing unit (CPU) 91 having a function of a light source lighting control means and a function of a lighting time limitation means is provided on the LED control board 90. In Embodiment 2, as shown in FIG. 6, the LED control board 90 is electrically connected only to a light emitting diode (LED) L.

Specifically, the LED control board 90 is electrically connected to the light emitting diode (LED) L via the LED connector 93. Further, the LED control board 90 is electrically connected to the lamp lighting switch S via the switch connector 94. The switch connector 94 has two pins (connection terminals). In this Embodiment 2, the LED connector 93 has two pins (connection terminals).

No. 1 pin (denoted as "1" in FIG. 6) and No. 2 pin (denoted as "2" in FIG. 6) of the LED connector 93 are connected to a light emitting diode (LED) L. Unlike the aforementioned Embodiment 1, the LED control board 90 is electrically connected only to the light emitting diode (LED) L. When the LED connector 93 is inserted into the LED control board 90, the No. 1 pin is electrically connected to the DC power supply of 14 V, and the No. 2 pin is electrically connected to the CPU 91 via the transistor. Further, in the same manner as in the aforementioned Embodiment 1, the DC power supply of 14 V is electrically connected to an AC/DC conversion board (not shown). After converting an AC voltage into a DC voltage of 14 V, a power is supplied to the light emitting diode (LED) L.

The No. 1 pin (denoted as "1" in FIG. 6) and the No. 2 pin (denoted as "2" in FIG. 6) of the switch connector 94 are connected to a lamp lighting switch S. In the same manner as in the aforementioned Embodiment 1 and the halogen lamp control board 80 shown in FIG. 5, by inserting the switch connector 94 into the LED control board 90, the No. 1 pin is electrically connected to a resistor connected to the DC power supply of 5 V in the middle and is electrically connected to the CPU 91. Note that the No. 2 pin is grounded.

Further, a No. 5 pin (denoted as "5" in FIG. 6) of the CPU 91 is grounded. When the CPU 91 is mounted on the LED control board 90, the No. 5 pin of the CPU 91 is pulled down by the grounding to be in a low logic state. In this way, when the CPU 91 is mounted on the LED control board 90, by detecting that the No. 5 pin of the CPU 91 has become the low logic state, it is detected that the CPU 91 is mounted on the LED control board 90, and it is automatically discriminated that the type of the detected light source is a light emitting diode (LED) L.

In FIG. 5 and FIG. 6, different symbols 81 and 91 are allotted to the CPUs. However, in actual, the same CPU is used in the halogen lamp control board (halogen lamp lighting circuit) 80 shown in FIG. 5 and the LED control board (LED lighting circuit) 90 shown in FIG. 6. Therefore, in the halogen lamp control board 80 and the LED control board 90, by reversely setting the logic state of the same one pin of the CPU, it is possible to automatically detect which board the CPU is mounted on.

Also in this Embodiment 2, the control in accordance with the control methods 1 to 4 described in the aforementioned Embodiment 1 is performed.

With respect to the functions and effects of the X-ray image capturing apparatus 1 according to this Embodiment 2 having the aforementioned configuration, the explanation is omitted since the functions and effects are the same as those in aforementioned Embodiment 1.

In this Embodiment 2, as shown in FIG. 5 and FIG. 6, the light source type discrimination means detects that the light source lighting control means (CPU) for lighting the light source (halogen lamp H or light emitting diode (LED) L in FIG. 5 and FIG. 6) is mounted on the control board dedicated to the light source (halogen lamp control board 80 and LED control board 90 in FIG. 5 and FIG. 6) (in FIGS. 5 and 6, it is detected that the No. 5 pin of the CPU has become the high logic state or the low logic state). In this Embodiment 2, by simply preparing control boards dedicated to light sources (lighting circuit dedicated to light source) by the number of types of light sources and mounting the same light source lighting control means (CPU) on the respective control boards, it is possible to discriminate the type of the light source.

EMBODIMENT 3

Hereinafter, Embodiment 3 of the present invention will be described with reference to the drawings. In Embodiment 3, X-ray image capturing is performed using the X-ray image capturing apparatus 1 shown in FIG. 1 which is the same as the aforementioned Embodiments 1 and 2, which will also be applied to the block diagram of FIG. 2.

In the aforementioned Embodiments 1 and 2, based on the result of the discrimination by the light source type discrimination means (control board in each Embodiments 1 and 2), the lighting time to be limited by the lighting time limitation means (CPU in each of Embodiments 1 and 2) was changed. However, in this Embodiment 3, the lighting time limitation means (CPU) is disabled when the light source is discriminated as a semiconductor light source like an LED by the result of the discrimination by the light source type discrimination means (control board). This is because of the following reasons. That is, the power consumption of an LED is about 10 W to 20 W, which is 1/10 to 1/5 of the power consumption of a halogen lamp. Therefore, even if the lighting time limitation means (CPU) itself is disabled to light the LED indefinitely, the LED is less likely to overheat.

The light source type discrimination means may be a control board as shown in FIG. 4 or a control board as shown in FIG. 5 and FIG. 6.

Also in this Embodiment 3, the control in accordance with the control methods 1 to 4 described in the aforementioned Embodiment 1 is performed. That is, in any of the control method 1 to the control method 4, when the light source is a semiconductor light source like an LED, the lighting time limitation means (CPU) itself is disabled.

For example, in the control method 1, in the case of a halogen lamp, the lighting was prohibited when the count has reached 600. However, in the case of an LED, it is lighted indefinitely by disabling the lighting time limitation means. Further, in the control method 2, in the case of a halogen lamp, the lighting was subjected to the temperature limitation after the consecutive 5-minute lighting. However, in the case of an LED, it is lighted indefinitely by disabling the lighting time limitation means.

Further, in the control method 3, in the case of a halogen lamp, the lamp was subjected to the temperature limitation after the consecutive 5-minute lighting until the device is reactivated. However, in the case of an LED, it is lighted indefinitely by disabling the lighting time limitation means. Further, in the control method 4, in the case of a halogen lamp, the lamp was subjected to the temperature limitation for 10 minutes after the consecutive 5-minute lighting so that the lighting is continued for 10 seconds by pressing the lighting button once. However, in the case of an LED, it is lighted indefinitely by disabling the lighting time limitation means. Alternatively, in the case of an LED, the LED is lighted for 30 seconds which is the same as before the temperature limitation by pressing the lighting bottom once by disabling the lighting time limitation means.

According to the X-ray image capturing apparatus 1 according to Embodiment 3 having the aforementioned configuration, in the same manner as in the aforementioned Embodiments 1 and 2, in addition to the light source (collimator lamp 29 in each Embodiment) for illuminating an irradiation field of radiation (X-ray in each Embodiment) with visible light (light) and a light source lighting control means (CPU in each Embodiment) for controlling the lighting of the light source (collimator lamp 29), a lighting time limitation means (built in the CPU in each Embodiment) for limiting the lighting time of the light source (collimator lamp 29) so as to be equal to or shorter than the predetermined temperature and a light source type discrimination means (control board in each Embodiment) for discriminating the type of the light source connected to the device body are provided. By limiting the lighting time of the light source (collimator lamp 29) by the lighting time limitation means (built in the CPU) so that the temperature of the device exterior becomes equal to or less than a predetermined temperature, overheating of the device exterior is prevented. Unlike the aforementioned Embodiments 1 and 2, in cases where the light source is discriminated as a semiconductor light source (e.g., LED) by the result of the discrimination obtained by discriminating the type of the light source connected to the device body with the light source type discrimination means (control board), the light source lighting control means (CPU) disables the lighting time limitation means (built into the CPU). The semiconductor light source is composed of a semiconductor light source with small heat generation, such as, e.g., a laser diode (LD) that emits phase-aligned visible light and an LED used in each Embodiment. Therefore, in cases where a semiconductor light source with small heat generation is actually connected, by disabling the lighting time limitation means (built in the CPU), the lighting time is set to be longer, so that the light source can be used continuously for a long time. On the other hand, in cases where a light source with large heat generation (for example, halogen lamp) other than a semiconductor light source is actually connected, by enabling the lighting time limitation means (built in the CPU), the lighting time is set to be short, so that overheating can be prevented. Therefore, in cases where there is no possibility of overheating of the exterior temperature by using a semiconductor light source with small heat generation, by disabling the lighting time limitation means (built in the CPU), it becomes possible to use the light source continuously for a long time. As a result, the risk of incorrectly carrying out the setting can be prevented, and the setting for switching light sources can be carried out automatically.

EMBODIMENT 4

Hereinafter, Embodiment 4 of the present invention will be described with reference to the attached drawings. In Embodiment 4, X-ray image capturing is performed using the X-ray image capturing apparatus 1 shown in FIG. 1 which is the same as the aforementioned Embodiments 1 to 3, which will also be applied to the block diagram of FIG. 2.

In the aforementioned Embodiments 1 and 2, based on the result of the discrimination by the light source type discrimination means (control board in each Embodiments 1 and 2), the lighting time limitation means (CPU in each of Embodiments 1 and 2) changes the lighting time to be changed. However, in Embodiment 4, the lighting power limitation means (CPU) changes the lighting time to be changed based on the result of the discrimination by the light source type discrimination means (control board in each of Embodiments 1 and 2). In other words, the limitation target is a lighting time of the light source in Embodiments 1 and 2, while the limitation target is a lighting power of the light source in Embodiment 4.

In the same manner as in Embodiment 3, the light source type discrimination means may be a control board as shown in FIG. 4 or a control board as shown in FIG. 5 and FIG. 6.

To change the lighting power of the light source which is a limitation target, for example, it is performed as follows. Normally, in the case of lighting a light source by a direct current, PWM (Pulse Width Modulation) control is performed. Therefore, in order to change the lighting power of the light source which is a limitation target, the duty ratio of the pulse width is changed.

In cases where a halogen lamp is connected, for example, after monitoring the lighting time with a timer, by shortening the ON (High) time in a step-by-step manner or by extending the OFF (Low) time in a step-by-step manner, the lighting power is lowered to prevent overheating. On the other hand, in cases where the LED is connected, for example, even after monitoring the lighting time with a timer, by making the ON (High) time longer than in the halogen lamp and shortening the ON (High) time in a step-by-step manner, or by making the OFF (Low) time shorter than in the halogen lamp and extending the OFF (Low) time in a step-by-step manner, the lowering rate of the lighting power is set to be low.

Other than the above, the lighting power may be changed by making the voltage (see the DC power supply voltage in the control board in FIG. 4 to FIG. 6) variable. In cases where a halogen lamp is connected, for example, after monitoring the lighting time with a timer, by lowering the voltage in a step-by-step manner, the lighting power is lowered to prevent overheating. On the other hand, in cases where the LED is connected, for example, even after monitoring the lighting time with a timer, by lowering the voltage in a step-by-step manner in a longer time than in a halogen lamp, or by gradually lowering the voltage with a higher voltage than in the halogen lamp, the lowering rate of the lighting power is set to be low.

According to the X-ray image capturing apparatus 1 of Embodiment 4 having the aforementioned configuration, in addition to the light source (collimator lamp 29 in each Embodiment) for illuminating an irradiation field of the radiation (X-ray in each Embodiment) with visible light (light) and a light source lighting control means (CPU in each Embodiment) for controlling the lighting of the light source (collimator lamp 29), a lighting power limitation means (built in each Embodiment) for limiting the lighting power of a light source (collimator lamp 29) so as to be equal to or lower than the predetermined temperature and a light source type discrimination means (control board in each Embodiment) for discriminating the type of the light source connected to the device body are provided. By limiting the lighting power of the light source (collimator lamp 29) with the lighting power limitation means (built in the CPU) so that the temperature of the device exterior becomes equal to or lower than a predetermined temperature, overheating of the device exterior can be prevented. Based on the result of the discrimination obtained by discriminating the type of the light source connected to the device body in the light source type discrimination means (control board), by changing the lighting power to be limited by the lighting power limitation means (built in the CPU) with the light source lighting control means (CPU), it is not necessary for a person, such as, e.g., an assembler at the time of the shipment or a serviceman at the time of the maintenance, to automatically carry out the setting for switching light sources (collimator lamp 29). Further, based on the result of the discrimination by the light type discrimination means (control board), the lighting source power control means (built in the CPU) changes the lighting power to be changed. As a result, the risk of incorrectly carrying out the setting can be prevented. For example, even if a light source with large heat generation (e.g., halogen lamp) is actually connected, the type of the light source is automatically discriminated as a connection target. For example, after monitoring the lighting time with a timer, overheating is prevented by lowering the lighting power to limit it. On the other hand, even if a light source with small heat generation (e.g., LED) is actually connected, by automatically discriminating the type of the light source as a connection target, even after monitoring the lighting time with a timer, the lowering rate of the lighting power is set to be low. Therefore, in cases where there is a possibility of overheating of the exterior temperature by using a light source with large heat generation, overheating is prevented. In cases where there is no possibility of overheating of the exterior temperature by using a light source with small heat generation, it is possible to set to the lowering rate of the lighting power to be low. As a result, this prevents the risk of incorrectly carrying out the setting, and the setting for switching light sources can be carried out automatically.

EMBODIMENT 5

Hereinafter, Embodiment 5 of the present invention will be described with reference to the attached drawings. In Embodiment 5, X-ray image capturing is performed using the X-ray image capturing apparatus 1 shown in FIG. 1 which is the same as the aforementioned Embodiments 1 to 4, which will also be applied to the block diagram of FIG. 2.

In the Embodiment 4, the lighting power which is limited by the lighting power limitation means (CPU) is changed based on the result of the discrimination by the light source type discrimination means (control board). However, in this Embodiment 5, in cases where the light source is discriminated as a semiconductor light source like an LED by the result of the discrimination by the light source type discrimination means (control board), the lighting time limitation means (CPU) is disabled. As described in the aforementioned Embodiment 3, this is because of the following reasons. That is, the power consumption of an LED is about 10 W to 20 W, which is ⅒ to ⅕ of the power consumption of a halogen lamp. Therefore, even if the lighting time limitation means (CPU) itself is disabled to light the LED indefinitely, the LED is less likely to cause overheating.

In the same manner as in Embodiments 3 and 4, the light source type discrimination means may be a control board as shown in FIG. 4 or a control board as shown in FIG. 5 and FIG. 6.

Disabling the lighting power limitation means (CPU) itself can be performed, for example, as follows. In the same manner as in the aforementioned Embodiment 4, in cases where a halogen lamp is connected, for example, after monitoring the lighting time with a timer, by shortening the ON (High) time in a step-by-step manner or by extending the OFF (Low) time in a step-by-step manner, the lighting power is lowered to prevent overheating. On the other hand, in cases where an LED is connected, for example, even after monitoring the lighting time with a timer, by performing PWM control with the same duty ratio as that before a temperature limitation by disabling the lighting power limitation means (CPU) itself, the setting is carried out without decreasing the lighting power. Or, for example, even after monitoring the lighting time with a timer, by disabling the lighting power limitation means (CPU) itself, the lighting power is set to be larger than that when the PWM control is performed without performing the PWM control.

In cases where the LED is connected, the lighting power limitation means (CPU) itself may be disabled from the beginning. By disabling the lighting power limitation means (CPU) itself from the beginning, PWM control is performed always with the same duty ratio. With this, the setting can be carried out without lowering the lighting power. Alternatively, by disabling the lighting power limitation means (CPU) itself from the beginning, PWM control is not performed from the beginning. With this, the lighting power is set to be larger than in the case of PWM control.

Other than the above, in the same manner as in the aforementioned Embodiment 4, in cases where a halogen lamp is connected, for example, after monitoring the lighting time with a timer, by lowering the voltage in a step-by-step manner, the lighting power can be lowered to prevent overheating. On the other hand, in cases where an LED is connected, for example, even after monitoring the lighting time with a timer, by performing PWM control with the same voltage as that before the temperature limitation by disabling the lighting power limitation means (CPU) itself, setting is carried out without lowering the lighting power.

According to the X-ray image capturing apparatus 1 according to Embodiment 5 having the aforementioned configuration, in the same manner as in the aforementioned Embodiment 4, in addition to the light source (collimator lamp 29 in each Embodiment) for illuminating an irradiation field of radiation (X-ray in each Embodiment) with visible light (light) and a light source lighting control means (CPU in each Embodiment) for controlling the lighting of the light source (collimator lamp 29), a lighting power limitation means (built in each Embodiment) for limiting the lighting power of a light source (collimator lamp 29) so as to be equal to or lower than the predetermined temperature and a light source type discrimination means (control board in each Embodiment) for discriminating the type of the light source connected to the device body are provided. By limiting the lighting power limitation means (built in the CPU) with the lighting power of the light source (collimator lamp 29) so that the temperature of the device exterior becomes equal to or lower than a predetermined temperature, overheating of the device exterior is prevented. Unlike the aforementioned Embodiment 4, in cases where the light source is discriminated as a semiconductor light source (e.g., LED) by the result of the discrimination obtained by discriminating the type of the light source connected to the device body with the light source type discrimination means (control board), the light source lighting control means (built-in CPU) disables the lighting time limitation means (CPU). As mentioned in the aforementioned Embodiment 3, the semiconductor light source is composed of a semiconductor light source with small heat generation, such as, e.g., an LD (laser diode) and an LED in each Embodiment. Therefore, in cases where a semiconductor light source with small heat generation is actually connected, by disabling the lighting time limitation means (built in the CPU), setting can be carried out without lowering the lighting power, or setting is carried out to be large. On the other hand, in cases where a light source (for example, halogen lamp) with large heat generation other than a semiconductor light source is actually connected, by enabling the lighting time limitation means (built in the CPU), the lighting power is lowered to thereby prevent overheating. Therefore, in cases where there is no possibility of overheating of the exterior temperature by using a semiconductor light source with small heat generation, by disabling the lighting power limitation means (built in the CPU), it is possible to carry out the setting without lowering the lighting power or carry out the setting to be large. As a result, the risk of incorrectly carrying out the setting is prevented, and the setting for switching light sources can be carried out automatically.

The present invention is not limited to the aforementioned embodiments, and can be modified as follows.

(1) In each of the aforementioned Embodiments, although the explanation was made by exemplifying an X-ray as radiation, it can also be applied to radiation other than an X-ray (for example, α ray, β ray, γ ray, etc.).

(2) In each of the aforementioned Embodiments, although the explanation was made by exemplifying an X-ray image capturing apparatus for performing X-ray image capturing as a radiography apparatus, the explanation is not limited to an X-ray image capturing apparatus for performing X-ray image capturing. The present invention can also be applied to, for example, an X-ray fluoroscope in which X-rays are irradiated at a weaker dose than X-ray image capturing to sequentially acquire multiple X-ray images and each X-ray image is displayed in real time (moving image display).

(3) In each of the aforementioned Embodiments, although the X-ray image capturing apparatus is an apparatus as shown in FIG. 1, as long as it is a radiography apparatus equipped with a radiation irradiation means (X-ray tube 22 in each Embodiment) to irradiate radiation to the subject, it may be a device that performs photographing or radiographic inspection only in a standing posture or may be a device that performs image capturing and radiographic inspection only in a recumbent posture. Further, it may be an apparatus that performs X-ray image capturing or radiographic inspection equipped with a tiltable table to which both a standing position and a recumbent posture can be applied.

(4) In each of the aforementioned Embodiments, although the explanation was made by exemplifying a flat panel type X-ray detector as an X-ray detector, the X-ray detector is not particularly limited as long as it is normally used such as an X-ray film and a CR.

(5) In each of the aforementioned Embodiments, the type of the light source is two types of a halogen halogen lamp and a light emitting diode (LED). However, the present invention may be applied to the case of switching to any one of three or more types of light sources using other light source such as a laser diode (LD).

(6) In each of the aforementioned Embodiments, as a light source, although a collimator lamp that illuminates the entire irradiation field adjusted by leaves of the collimator was used as a light source, the light source is not limited to a collimator lamp as long as it is a light source that illuminates the irradiation field of radiation with visible light. A line marker that illuminates the reference line (for example, the center line) in the irradiation field with visible light may be used by irradiating line-like visible light. Also, both a collimator lamp and a line marker may be used.

(7) In each of the aforementioned Embodiments, although a halogen lamp filled with a halogen gas is used as a light source with large heat generation, an incandescent lamp filled with a gas other than a halogen gas may be used.

(8) In each of the aforementioned Embodiments, although a light emitting diode (LED) is used as a semiconductor light source with small heat generation, a laser diode (LD) that emits phase-aligned visible light may be used.

(9) In each of the aforementioned Embodiments, although the central processing unit (CPU) is exclusively used for the function of the light source lighting control means, the function of lighting time/lighting power limitation means may be built in, the function of source lighting control means and the function of lighting time/lighting power limitation means may be provided independently.

Figure 7:
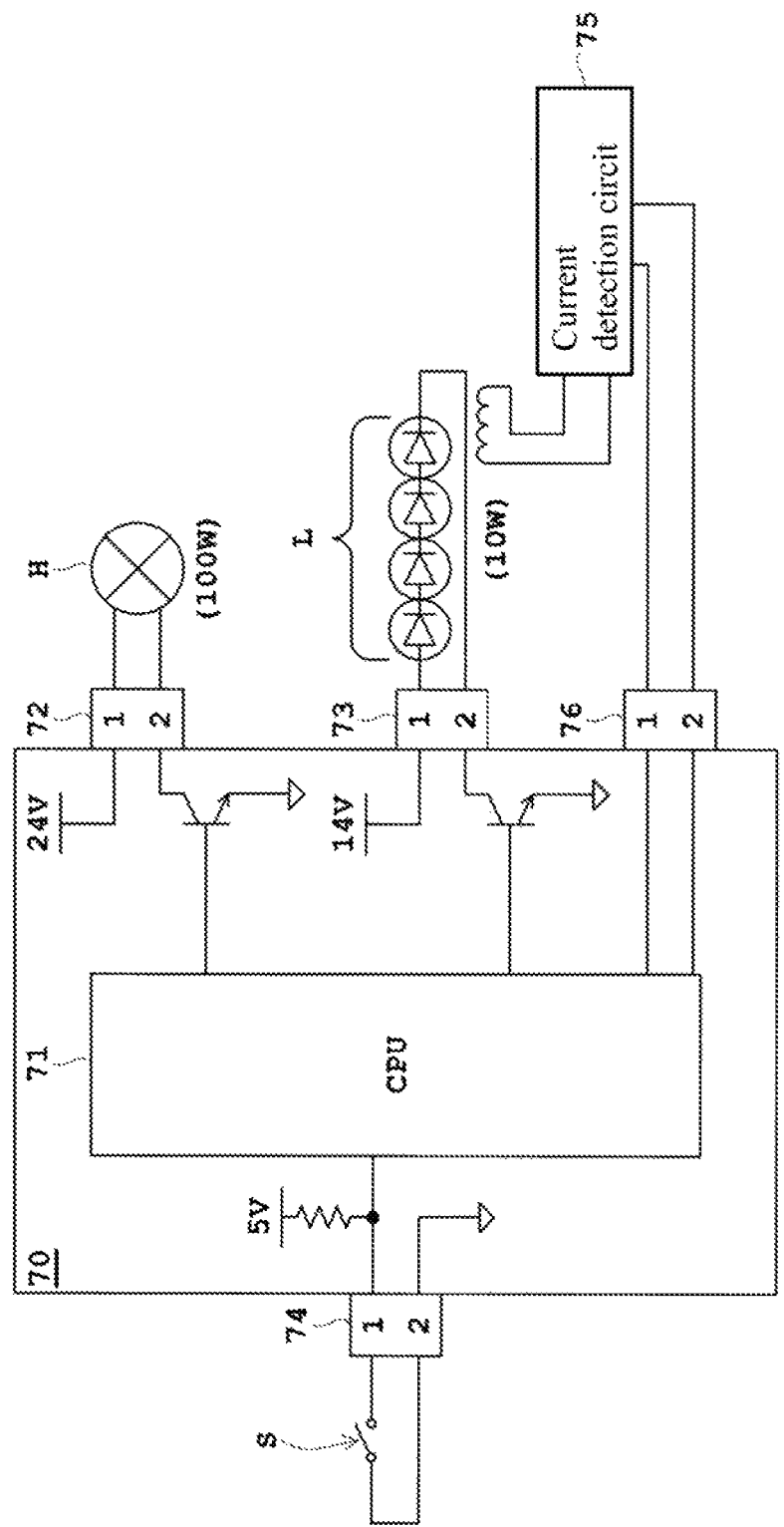
FIG. 7 is a control board and peripheral circuits according to a modified Embodiment for explaining a light source type discrimination means.

(10) In each of the aforementioned Embodiments, the light source type discrimination means is a control board as shown in FIG. 4 to FIG. 6, but it is not limited to the control board. For example, it may be configured such that an optical sensor for optically detecting the presence or absence of a connection by a connector is provided, the optical sensor and the CPU are connected, and the light source type discrimination means is configured by the CPU. Other than the above, it also may be configured such that it is provided with a current detection circuit that detects the presence or absence of current flowing through a cable connected to the light source connected to the device body, the current detection circuit and the CPU are connected, and the light source type discrimination means is configured by the CPU. Specifically, as shown in FIG. 7, it is provided with a current detection circuit 75 for detecting the presence or absence of a current flowing through the cable connected to the light emitting diode (LED) L, and the CPU 71 is electrically connected to the current detection circuit 75 via the current detection circuit connector 76. In cases where the current detection circuit 75 detects that a current is flowing through the cable connected to the light emitting diode (LED) L, the light source connected to a device body detects the light emitting diode (LED) L, and it is automatically discriminated that the type of the detected light source is a light emitting diode (LED) L. On the other hand, in cases where the current detection circuit 75 detects that a current is not flowing through the cable connected to the light emitting diode (LED) L, the light source connected to a device body detects the light emitting diode (LED) L, and it is automatically discriminated that the type of the detected light source is a halogen lamp H. A current detection circuit for detecting the presence or absence of a current flowing through the cable connected to the halogen lamp may be provided.

DESCRIPTION OF REFERENCE SYMBOLS

1: X-ray image capturing apparatus
22: X-ray tube
28: control unit
29: irradiation field lamp (collimator lamp)
70, 80, 90: control board
71, 81, 91: central processing unit (CPU)
H: halogen lamp
L: light emitting diode (LED)
M: subject

The invention claimed is:

1. A radiography apparatus equipped with a radiation source configured to irradiate radiation toward a subject, the radiography apparatus comprising:
 a light source configured to illuminate an irradiation field of the radiation with visible light; and
 a control board configured to:
  control lighting of the light source;
  limit a lighting time of the light source; and
  distinguish a type of the light source connected to a device body,
 wherein the control board changes the lighting time based on a result of the distinguishing.

2. The radiography apparatus as recited in claim 1, wherein the control board is configured to detect that the light source is connected to the device body.

3. The radiography apparatus as recited in claim 1, wherein the control board is dedicated to the type of the light source for lighting the light source.

4. The radiography apparatus as recited in claim 1, wherein the control board is configured to limit a lighting time of the light source to prevent the radiography apparatus from exceeding a predetermined temperature.

5. A radiography apparatus equipped with a radiation source configured to irradiate radiation toward a subject, the radiography apparatus comprising:
 a light source configured to illuminate an irradiation field of the radiation with visible light; and
 a control board configured to:
  control lighting of the light source;
  limit a lighting time of the light source; and
  distinguish a type of the light source connected to a device body, wherein the control board disables the lighting time limitation when the light source is distinguished as a semiconductor light source by a result of the distinguishing.

6. The radiography apparatus as recited in claim 5, wherein the control board detects that the light source is connected to the device body.

7. The radiography apparatus as recited in claim 5, wherein the control board is dedicated to the type of the light source for lighting the light source.

8. The radiography apparatus as recited in claim 5, wherein the control board is configured to limit a lighting time of the light source to prevent the radiography apparatus from exceeding a predetermined temperature.

9. A radiography apparatus equipped with a radiation source configured to irradiate radiation toward a subject, the radiography apparatus comprising:
   a light source configured to illuminate an irradiation field of the radiation with visible light; and
   a control board configured to:
      control lighting of the light source;
      limit lighting power of the light source; and
      distinguish a type of the light source connected to a device body,
   wherein the control board changes the lighting power based on a result of the distinguishing.

10. The radiography apparatus as recited in claim 9, wherein the control board detects that the light source is connected.

11. The radiography apparatus as recited in claim 9, wherein the control board is dedicated to the type of the light source for lighting the light source.

12. The radiography apparatus as recited in claim 9, wherein the control board is configured to limit a lighting power of the light source to prevent the radiography apparatus from exceeding a predetermined temperature.

13. A radiography apparatus equipped with a radiation source for irradiating radiation toward a subject, the radiography apparatus comprising:
   a light source configured to illuminate an irradiation field of radiation with visible light; and
   a control board configured to:
      control lighting of the light source;
      limit lighting power of the light source; and
      distinguish a type of the light source connected to a device body,
   wherein the control board disables the lighting power limitation when the light source is distinguished as a semiconductor light source by a result of the distinguishing.

14. The radiography apparatus as recited in claim 13, wherein the control board detects that the light source is connected.

15. The radiography apparatus as recited in claim 13, wherein the control board is dedicated to the type of the light source for lighting the light source.

16. The radiography apparatus as recited in claim 13, wherein the control board is configured to limit a lighting power of the light source to prevent the radiography apparatus from exceeding a predetermined temperature.

\* \* \* \* \*